United States Patent [19]

Mizukami et al.

[11] Patent Number: 5,717,110
[45] Date of Patent: Feb. 10, 1998

[54] UCH15 COMPOUNDS

[75] Inventors: Tamio Mizukami, Machida; Akira Asai, Sagamihara; Yoshinori Yamashita, Machida; Hirofumi Nakano, Machida; Shingo Kakita, Machida; Youichi Uosaki, Machida; Keiko Ochiai, Ebina; Tadashi Ashizawa, Numazu; Akira Mihara, Machida, all of Japan

[73] Assignee: Kyowa Hakko Kogyo Co., Ltd., Tokyo, Japan

[21] Appl. No.: 836,314

[22] PCT Filed: Sep. 11, 1996

[86] PCT No.: PCT/JP96/02587

§ 371 Date: May 12, 1997

§ 102(e) Date: May 12, 1997

[87] PCT Pub. No.: WO97/10208

PCT Pub. Date: Mar. 20, 1997

[30] Foreign Application Priority Data

Sep. 12, 1995 [JP] Japan .................. 7/234318

[51] Int. Cl.⁶ ........................... C07D 207/00
[52] U.S. Cl. ........................... 548/518
[58] Field of Search ............... 548/518; 514/422

[56] References Cited

U.S. PATENT DOCUMENTS 4,766,142  8/1988  Arcamone et al. .......... 514/422
5,175,182  12/1992  Mongelli et al. ........... 514/428
5,472,976  12/1995  Animati et al. ............ 514/422

OTHER PUBLICATIONS

JACS, 73, 341 (1951).

Cancer Res. suppl. 3, 18 (1951).

Cancer Chemother. Rep., 18, 15 (1962).

Nature, 203, 1064 (1964).

Antimicrob. Ag. Chemother., 5, 593 (1965).

*Primary Examiner*—Raymond Henley, III
*Attorney, Agent, or Firm*—Antonelli, Terry, Stout, & Kraus, LLP

[57] ABSTRACT

This invention relates to UCH15 compounds of the formula (I):

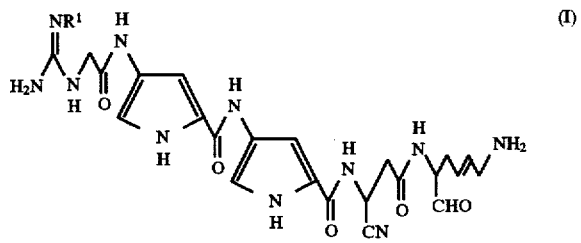

wherein $R^1$ represents a hydrogen atom or a hydroxyl group.

1 Claim, No Drawings

UCH15 COMPOUNDS

This application is a 371 of PCT/JP96/02587 filed Sep. 11, 1996.

TECHNICAL FIELD

The present invention relates to UCH15 compounds which have antibacterial and antitumor activities and, therefore, are useful as antibacterial and antitumor agents.

BACKGROUND ART

Distamycin A which is represented by the formula (II):

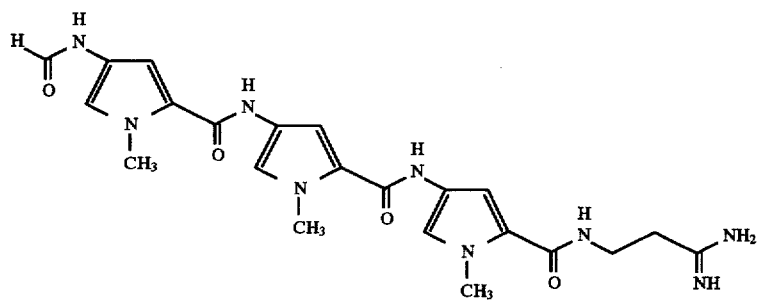

and which has antibacterial and antiviral activities is known [see Cancer Chemother. Rep., 18, 15 (1962); Nature, 203, 1064 (1964); Antimicrob. Ag. Chemother., 5, 593 (1965)]. Also known is netropsin of the formula (III):

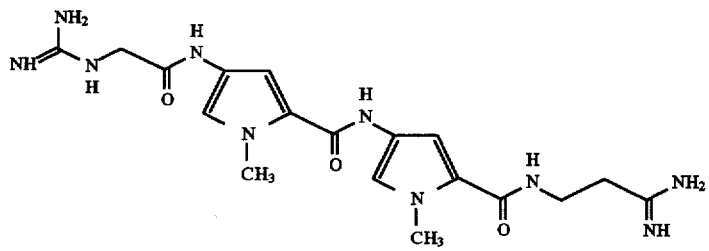

[see JACS, 73, 341 (1951); Cancer Res., 3, 18 (1957)].

DISCLOSURE OF THE INVENTION

According to the present invention, provided are UCH15 compounds which are represented by the following formula (I) and have antibacterial and antitumor activities:

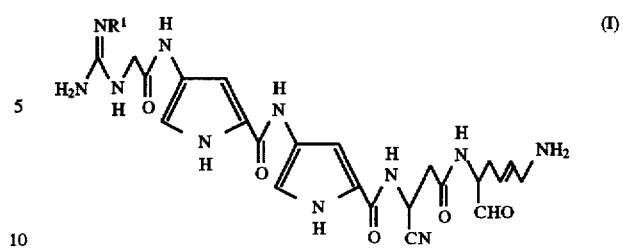

wherein $R^1$ represents a hydrogen atom or a hydroxyl group.

Now, the present invention is described in detail hereinafter.

UCH15 compounds include, for example, a compound of the formula (Ia):

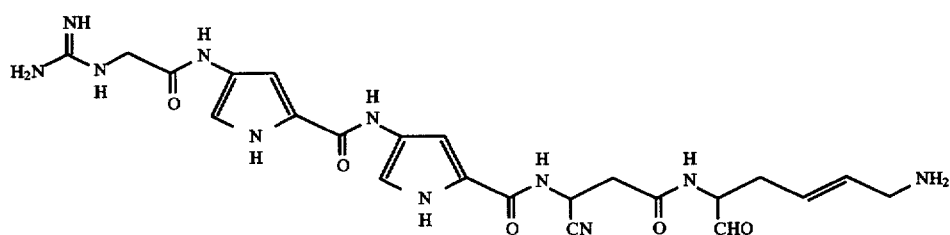

(Ia)

which is hereinafter referred to as UCH15A, and a compound of the formula (Ib):

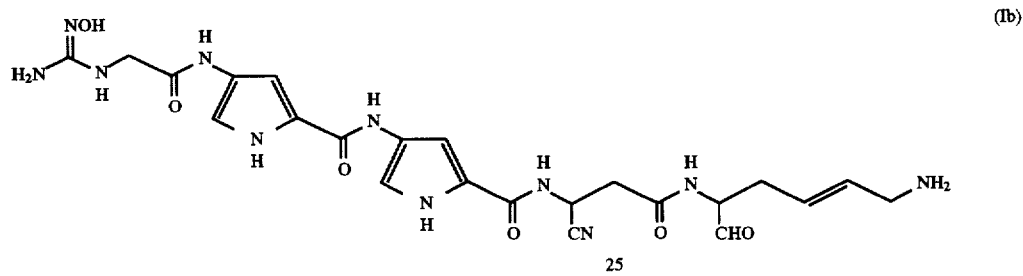

(Ib)

which is hereinafter referred to as UCH15B.

In the formula (I), the aldehyde group of UCH15A and UCH15B is believed to exist as such in aprotic solvents, but is mostly converted into a hydrated form in aqueous solutions and is mostly either in an alcohol-added hemiacetal or acetal form in alcoholic solutions, as in the following reaction formulae:

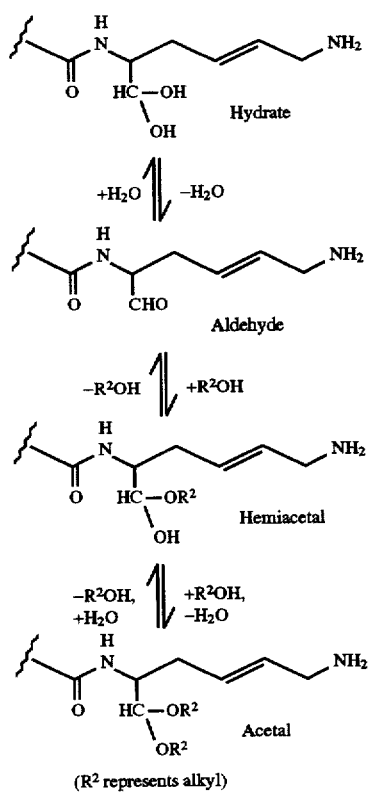

($R^2$ represents alkyl)

wherein $R^2$ represents an alkyl group.

Since these forms are extremely easily converted into an aldehyde group, the hydrate, hemiacetal and acetal forms are chemically equivalent to the aldehyde group.

In the formula (Ia), the guanidino group of UCH15A can be represented as follows:

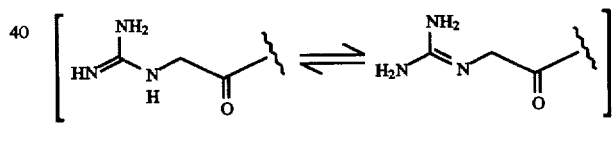

These groups represent the limiting structures of a single chemical species, and are in a resonance hybrid. As being chemically equivalent to each other, these groups can not be differentiated from each other.

Also in the formula (Ib), the hydroxyguanidino group of UCH15B can be represented as follows:

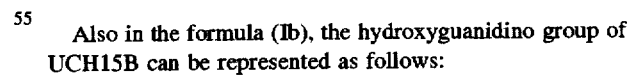

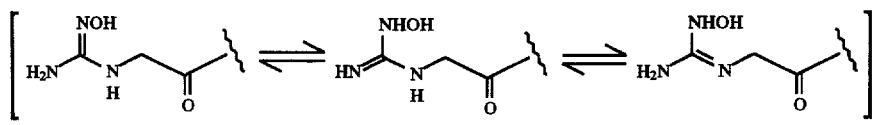

Also as being chemically equivalent to each other, these groups can not be differentiated from each other.

In addition, the aldehyde group of UCH15A and UCH15B may be racemated through keto-enol equivalent conversion in solutions, as follows:

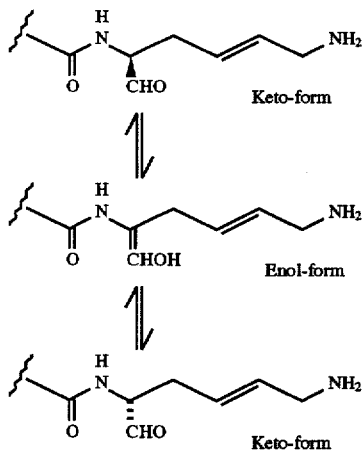

In fact, in the $^1$H NMR spectra of UCH15 in a solution of heavy water ($D_2O$) or $CD_3OD$, the hydrogen to which the aldehyde group (in fact, this aldehyde group is observed as the hydrated hemiacetal form thereof as in the above) is bound gave time-dependently attenuating or disappearing signals. This phenomenon results from the substitution of said hydrogen atom with a heavy hydrogen atom, as in the following reaction formulae, and indicates that a minor amount of the aldehyde group exists even in protic solvents and that said aldehyde group is in keto-enol equivalency.

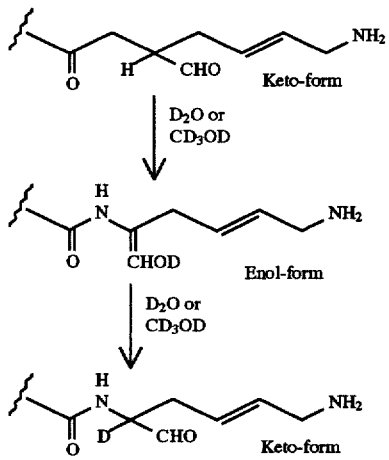

It is expected that UCH15A and UCH15B may naturally be produced in the form of a certain diastereomer by UCH15-producing microbes. In a solvent, however, since said diastereomer is easily converted into another diastereomer, UCH15A and UCH15B are to be collected as a mixture of each two diastereomers that are substantially impossible to separate. In addition, the ratios of the diastereomers of the two compounds are changed depending on the method and conditions for isolating and purifying said compounds.

For convenience' sake, UCH15 compounds of the present invention may be represented by the above-mentioned formula (I), but shall include their additives with, for example, water, and even their tautomers and diastereomers as being chemically equivalent to each other, as so mentioned hereinabove.

Now, the physicochemical characteristics of UCH15A and UCH15B are shown below. As so mentioned hereinabove, these compounds are a non-stoichiometric mixture of two diastereomers. The data mentioned below are of the samples obtained according to the method of Example 1 to be mentioned hereinafter, and each sample is in the form of a mixture (trifluoroacetate) of diastereomers of about 1:1.

Physicochemical Properties of UCH15A trifluoroacetate (1) Appearance: white solid (2) Molecular formula: $C_{23}H_{29}N_{11}O_5$ as free base aldehyde (3) Molecular weight: 539 as free base aldehyde (4) FAB mass spectrum (positive mode; solvent: water; matrix: m-NBA):

m/z amu 558 $(M+H_2O+H)^+$: pseudo-molecular ion peak of free base hydrate (M: molecular weight of free base aldehyde)

(5) High-resolution FAB mass spectrum (positive mode; solvent: water; matrix: m-NBA):

m/z amu 558.2518Δ–1.9 mmu (as $C_{23}H_{32}N_{11}O_6$)

(6) UV absorption spectrum (aqueous solution):

λmax nm (ε: as di-trifluoroacetate) 297 (29,600), 233 (26, 300)

(7) IR absorption spectrum (KBr method):

vmax cm$^{-1}$ 3344 (broad), 3284 (sh), 2970, 2939, 1674, 1632 (sh), 1587 (sh), 1558, 1539, 1435, 1404, 1203, 1136, 839, 802, 723

(8) $^1$H NMR spectrum [400 MHz, $D_2O$ solution, 30° C., internal standard DOH (→4.77 ppm)]:

For the individual hydrogen atoms giving separated signals for two diastereomers, said signals are shown separately; but for the others not giving separated signals, said signals are not specifically differentiated. Since the sample is a mixture of diastereomers of about 1:1, the integrated value represented by 1H indicates one hydrogen atom of each diastereomer.

δ ppm [integration, multiplicity, coupling constant (Hz)]
7.4–7.3 (4H, m) , 7.0–6.9 (4H, m) , 5.80 (1H, m), 5.65 (1H, m), 5.56 (1H, m), 5.32 (1H, m), 5.27 (2H, m), 5.03 (2H, m), 4.13 (4H, m), 3.98 (1H, m), 3.94 (1H, m), 3.69 (1H, m), 3.63 (2H, m), 3.48 (1H, m), 3.2–3.0 (4H, m), 2.50 (1H, m), 2.45 (1H, m), 2.33 (1H, m), 2.26 (1H, m)

(9) $^{13}$C NMR spectrum (100 MHz, $D_2O$ solution, 30° C., internal standard TSP):

For the individual carbon atoms giving separated signals for two diastereomers, said signals are shown separately; but for those giving overlapped signals, said signals are represented by x2 in parentheses. δ ppm (multiplicity) 170.95 (s, x2), 168.50 (s, x2), 164.02 (s), 163.67 (s), 162.84 (s), 162.66 (s), 158.48 (s, x2), 133.37 (d), 133.33 (d), 123.90 (s, x2), 123.49 (d), 123.42 (s), 123.26 (d), 122.80 (s, x2), 122.74 (s), 122.72 (s), 122.65 (s), 119.21 (s), 119.17 (s), 116.80 (d, x2), 116.04 (d), 115.80 (d), 106.41 (d, x2), 105.26 (d, x2), 90.81 (d), 90.79 (d), 55.05 (d), 55.01 (d), 44.65 (t, x2), 38.78 (t), 38.74 (t), 38.61 (d, x2), 36.97 (t), 36.85 (t), 27.91 (t), 27.75 (t)

(10) Solubility:
Soluble in water, methanol, and dimethylsulfoxide (DMSO); but insoluble in hexane, chloroform, and ethyl acetate.

(11) Color reaction:
Positive to iodine reagents and ninhydrin reagents.

(12) Thin layer chromatography: Rf value 0.4
Thin layer: thin ODS layer (HPTLC plate Art. 13124, manufactured by Merck Co.)
Developing solvent: aqueous solution of 20% acetonitrile/0.5 % trifluoroacetic acid (1:1, v/v) After having been developed, the spots of UCH15A are detectable with iodine or ninhydrin reagents.

Physicochemical Properties of UCH15B Trifluoroacetate (1) Appearance: white solid
(2) Molecular formula: $C_{23}H_{29}N_{11}O_6$ as free base aldehyde
(3) Molecular weight: 555 as free base aldehyde
(4) Specific rotation: $[\alpha]D^{23}=+5.2°$ (c=0.05, $H_2O$)
(5) FAB mass spectrum (positive mode; solvent: water; matrix: m-NBA):
m/z amu 574 $(M+H_2O+H)^+$; pseudo-molecular ion peak of free base hydrate (M: molecular weight of free base aldehyde)
(6) High-resolution FAB mass spectrum (positive mode; solvent: water; matrix: m-NBA):
m/z amu 574.2487Δ+0.1 mmu (as $C_{23}H_{32}N_{11}O_7$)
(7) UV absorption spectrum (aqueous solution):
λmax nm (ε: as di-trifluoroacetate) 297 (32, 500), 232 (27, 000)
(8) IR absorption spectrum (KBr method):
vmax $cm^{-1}$ 3417 (broad), 3284 (sh), 2958, 2927, 1716, 1653, 1645, 1638, 1596 (sh), 1558, 1539, 1404, 1225
(9) $^1H$ NMR spectrum (400 MHz, $D_2O$ solution, 5° C., internal standard TSP):
For the individual hydrogen atoms giving separated signals for two diastereomers, said signals are shown separately; but for the others not giving separated signals, said signals are not specifically differentiated. Since the sample is a mixture of diastereomers of about 1:1, the integrated value represented by 1H indicates one hydrogen atom of each diastereomer.
δ ppm [integration, multiplicity, coupling constant (Hz)] 7.3 (2H, m), 7.2 (2H, m), 6.9 (2H, m), 6.8 (2H, m), 5.77 (1H, m), 5.60 (1H, m), 5.56 (1H, m), 5.27 (1H, m), 5.23 (2H, m), 5.01 (2H, m), 4.16 (4H, s), 3.95 (1H, m), 3.93 (1H, m), 3.68 (1H, m), 3.60 (1H, m), 3.57 (1H, m), 3.40 (1H, m), 2.9–3.1 (4H, m), 2.48 (1H, m), 2.40 (1H, m), 2.34 (1H, m), 2.26 (1H, m)

(10) $^{13}C$ NMR spectrum (100 MHz, $D_2O$ solution, 5° C., internal standard TSP):
For the individual carbon atoms giving separated signals for two diastereomers, said signals are shown separately; but for those giving overlapped signals, said signals are represented by x2 in parentheses. δ ppm (multiplicity) 170.85 (s, x2), 167.66 (s), 167.52 (s), 162.53 (s), 162.35 (s), 160.74 (s), 160.63 (s), 159.96 (s), 159.94 (s), 133.20 (d, x2), 123.63 (s), 123.58 (s), 123.50 (d), 123.47 (s), 123.44 (s), 123.19 (d), 122.89 (s), 122.86 (s), 122.29 (s), 122.19 (s), 118.94 (s), 118.88 (s), 115.92 (d), 115.86 (d), 115.33 (d), 115.20 (d), 105.43 (d, x2), 104.38 (d), 104.26 (d), 90.62 (d), 90.60 (d), 54.88 (d), 54.85 (d), 44.11 (t, x2), 38.70 (t), 38.56 (d), 38.44 (t), 38.38 (d), 36.76 (t), 36.61 (t), 27.91 (t), 27.66 (t)

(11) Solubility:
Soluble in water, methanol, and dimethylsulfoxide (DMSO); but insoluble in hexane, chloroform, and ethyl acetate.

(12) Color reaction:
Positive to iodine reagents and ninhydrin reagents.

(13) Thin layer chromatography: Rf value 0.5
Thin layer: thin ODS layer (HPTLC plate Art. 13124, manufactured by Merck Co.)
Developing solvent: aqueous solution of 20% acetonitrile/0.5 % trifluoroacetic acid (1:1, v/v)
After having been developed, the spots of UCH15B are detectable with iodine or ninhydrin reagents.

The apparatus used for the measurement are as follows: Mass spectra: JMS-HX/110A Mass Spectrograph (Nippon Electronics Co.), UV absorption spectrum: UV-2200 Spectrophotometer (Shimadzu Seisaku-sho Co.), IR absorption spectrum: JIR-RFX3001 Infrared Spectrophotometer (Nippon Electronics Co.), NMR spectra: JNM-A400 NMR Spectrometer (Nippon Electronics Co.), Specific rotation: DIP-370 Digital Polarimeter (Nippon Bunko Co.).

Now, a process for producing UCH15 compounds is described below.

UCH15 compounds can be produced by cultivating microorganisms, which belong to the genus Streptomyces and are capable of producing UCH15 compounds, in a medium to allow them to produce and accumulate UCH15 compounds in the culture, and collecting the UCH15 compounds from the culture.

As the microorganisms capable of producing UCH15 compounds, any strain may be employed so long as it belongs to the genus Streptomyces and has the ability to produce UCH15 compounds. Further, variants, for example, those obtained by artificially mutagenizing the above-mentioned strain by, for example, UV irradiation, X-ray irradiation or treatment with mutagenic agents, as well as spontaneously mutagenized ones can also be used so long as they are capable of producing UCH15 compounds. For example, microorganisms which the present inventors have newly isolated from soil as collected in Aichi-ken of Japan are preferably used in the present invention. The microorganisms thus isolated is hereinafter referred to as UCH15 strain.

The microbiological properties of the UCH15 strain are mentioned below. To determine these properties, the method as recommended by the International Streptomyces Project for the identification of the species of Streptomyces was applied [see E. B. Shirling & D. Gottlieb.; Int. J. Syst. Bacteriol., 16, 313–340 (1966)]. The diaminopimelic acid isomer in the hydrolysate of the whole cells was identified in accordance with the method of B. Becker et al. [see Appl. Microbiol., 12, 421–423 (1964)]. An optical microscope was used in the morphological observation. In particular, the morphology of the spore surface was observed with a scanning electron microscope. To express the names of colors, Color Harmony Manual [Container Corporation of America, 4th Ed. (1958)] was referred to.

1. Morphological Properties:
   1) Hyphae
      Formation of aerial hyphae: Observed.
      Fragmentation and motility of aerial hyphae: Not observed.
      Fragmentation and motility of substrate hyphae: Not observed.
   2) Spores
      Formation and location of spores: Formed on aerial hyphae.
      Formation and location of sporangia: Not observed.
      Number of spores in chain formed at the end of the sporophore: 10 or more.
      Form of spore chains: Linear or curvaceous.
      Characteristics of spores:
         Surface structure: Smooth.
         Shape and size: Bacillus, about 0.8–1.0 μm 0.9–1.3 μm.
      Motility of spores and presence of flagella: Not observed.
   3) Others
      Chlamydospores: Not observed.
      Synnemata: No observed.
      Pseudosporangia: No observed.
      Branching mode of hyphae: Simple branching.

2. Cultural characteristics:
   The UCH15 strain moderately or vigorously grows on synthetic and natural media commonly employed in the art. Its substrate hyphae are brown to pale gray. On some media, the strain may produce a pale brown, soluble pigment.

The following data show the growth and color characteristics observed when the strain was cultivated on various media at 28° C. for 14 days.

1) Sucrose nitrate agar medium
      Growth: Excellent.
      Color of Substrate hyphae: Sand (2ec).
      Formation of aerial hyphae and color thereof:
         Vigorous; beige (3ig).
      Soluble pigment: None.
   2) Glucose asparagine agar medium
      Growth: Excellent.
      Color of Substrate hyphae: Shell pink (5ba).
      Formation of aerial hyphae and color thereof:
         Vigorous; white (a)—silver gray (3fe).
      Soluble pigment: None.
   3) Glycerol asparagine agar medium
      Growth: Excellent.
      Color of Substrate hyphae:
         Light ivory (2ca)—mustard tan (21g).
      Formation of aerial hyphae and color thereof:
         Vigorous; white (a)—ash (5fe)
      Soluble pigment: Produced, but a little (pale yellow).
   4) Starch inorganic salt agar medium
      Growth: Excellent.
      Color of Substrate hyphae:
         Bamboo (2gc)—straight tan (2ig).
      Formation of aerial hyphae and color thereof:
         Vigorous; crowd pink (7cb)—ash (5fe).
      Soluble pigment: Produced, but a little (pale yellow).
   5) Tyrosine agar medium
      Growth: Excellent.
      Color of Substrate hyphae: Silver gray (3fe).
      Formation of aerial hyphae and color thereof:
         Vigorous; rose tope (6ig)—tope gray (7ih).
      Soluble pigment: None.
   6) Vegetative agar medium
      Growth: Excellent.
      Color of Substrate hyphae: Light mustard tan (2ie).
      Formation of aerial hyphae and color thereof:
         Relatively poor; white (a).
      Soluble pigment: Produced, but a little (ocher).
   7) Yeast malt agar medium
      Growth: Excellent.
      Color of Substrate hyphae:
         Bamboo (2gc)—mustard brown (2pl).
      Formation of aerial hyphae and color thereof:
         Vigorous; white (a)—ash (5fe).
      Soluble pigment: Produced (ocher).
   8) Oatmeal agar medium
      Growth: Excellent.
      Color of Substrate hyphae: Covert tan (2ge).
      Formation of aerial hyphae and color thereof:
         Vigorous; rose tope (5ig).
      Soluble pigment: Produced, but a little (brown).

3. Physiological Properties:
   The growth temperature range was determined after 10 days of cultivating and the other observations were made after 2 to 3 weeks of cultivation at 28° C.
   1) Growth temperature range: 11.0°–42.0° C.
   2) Liquefaction of gelatin: Not observed.
   3) Hydrolysis of starch: positive.
   3) Coagulation and peptonization of skim milk powder: Peptonized.
   5) Melanoid pigment formation:
      (1) Peptone yeast iron agar medium: Formed.
      (2) Tyrosine agar medium: Negative.
   6) Utilization of carbon source:
      A Pridham and Gottlieb agar medium was used as the basal medium. Hereinafter, "+" means that the strain utilizes the carbon source, while "−" means that the strain does not utilize the carbon source.

|  |  |
|---|---|
| L-arabinose: | + |
| D-xylose: | + |
| D-glucose: | + |
| Sucrose: | + |
| Raffinose: | + |
| D-fructose: | + |
| Rhamnose: | + |
| Inositol: | + |
| D-mannitol: | + |

4. Chemical Classification:
   Optical isomer of diaminopimelic acid in cell: LL-form.
   Based on its microbiological properties mentioned above, this strain is classified into the genus Streptomyces.

Accordingly, the present inventors have named this strain Streptomyces sp. UCH15 and have deposited the strain at the National Institute of Bioscience and Human-Technology, Agency of Industrial Science and Technology (1–3, Higashi 1-chome, Tsukuba-shi, Ibaraki-ken 305, Japan) since Apr. 25, 1995 under the accession number FERM BP-5082.

To culivate the microorganisms capable of producing UCH15 compounds of the present invention, any conventional methods for cultivating actinomycetes may be employed. As the medium, either a synthetic medium or a natural one may be used so long as it contains appropriate carbon sources, nitrogen sources and inorganic substances optionally along with any other minor components, which can be assimilated by actinomycetes.

Examples of the carbon sources include, for example, starch, dextrin, sucrose, glucose, mannose, fructose, raffinose, rhamnose, inositol, lactose, xylose, arabinose, mannitol, and molasses. Any of these substances or a combination thereof may be used. Hydrocarbons, alcohols, and organic acids may also be used, depending on the assimilability of the microorganisms employed.

Examples of the nitrogen sources include, for example, ammonium chloride, ammonium nitrate, ammonium sulfate, sodium nitrate, urea, peptone, meat extract, yeast extract, dry yeast, corn steep liquor, soybean powder, and casamino acid. Any of these substances or a combination thereof may be used.

Examples of the inorganic salts include, for example, sodium chloride, potassium chloride, magnesium sulfate, calcium carbonate, potassium dihydrogenphosphate, ferrous sulfate, calcium chloride, manganese sulfate, zinc sulfate, and copper sulfate. Any of these substances or a combination thereof may be used.

Examples of the minor components include vitamins such as biotin, thiamine and nicotinic acid; and amino acids such as β-alanine and glutamic acid. Any of these substances or a combination thereof may be used.

As the method of cultivating the microorganisms, liquid culture is preferred, and submerged spinner culture is more preferred. The cultivation is carried out at a temperature of 16° to 37° C., preferably 25° to 32° C., and at pH 4 to 10, preferably pH 6 to 8. In usual, the cultivation is completed within 1 to 7 days, and thus the intended UCH15 compounds are produced and accumulated in the cultured medium and the cells. The pH value of the medium is regulated by adding aqueous ammonia, a solution of ammonium carbonate, etc.

The UCH15 compounds thus accumulated in the culture may be isolated and purified in accordance with the methods commonly employed for the isolation and purification of microbial metabolites from cultures. For example, the culture is filtered to separate the cells from the cultured medium. Then, the cells are extracted with a solvent such as chloroform or acetone. Next, the extract is combined with the cultured medium and passed through a column packed with a polystyrene adsorbent, for example, Diaion HP20 (manufactured by Mitsubishi Chemical Industries, Ltd.) by which the active component is adsorbed. After eluting with, for example, methanol or acetone, the eluate is concentrated and subjected to, for example, ODS column chromatography or high performance liquid chromatography to thereby give UCH15 compounds. During the cultivation, isolation and purification steps, UCH15 compounds can be detected by an iodine staining reagent after employing thin layer ODS chromatography.

The biological activities of UCH15 compounds are mentioned below, with reference to the following Test Examples.

Test Example 1

Antibacterial Activity on Various Bacteria

Table 1 shows the minimum inhibitory concentrations (MIC) of UCH15 compounds on various bacteria. These antibacterial activities were determined by the agar dilution method with the use of a medium (pH 7) comprising 3 g/liter of bactotryptone (manufactured by Difco), 3 g/liter of meat extract, 1 g/liter of yeast extract, 1 g/liter of glucose and 16 g/liter of agar.

TABLE 1

| Bacteria Tested | Minimum Inhibitory Concentration (µg/ml) | |
|---|---|---|
| | UCH15A | UCH15B |
| Staphylococcus aureus ATCC 6538P | 2.6 | 5.2 |
| Enterococcus hirae ATCC 10541 | 2.6 | 10.4 |
| Bacillus subtilis No. 10707 | 0.08 | 0.33 |
| Klebsiella pneumoniae ATCC 10031 | 0.02 | 0.04 |
| Escherichia coli ATCC 26 | 0.16 | 0.08 |
| Pseudomonas aeruginosa Bin H No. 1 | >50 | >50 |
| Salmonella choleraesuis ATCC 9992 | 0.16 | 0.33 |
| Proteus vulgaris ATCC 6897 | 0.16 | 0.33 |
| Shigella sonnei ATCC 9290 | 0.16 | 0.33 |
| Candida albicans ATCC 10231 | 10.4 | >41.7 |

Test Example 2

Growth Inhibition on Hela S3 Cells

Into each well of a 96-well microtiter plate was pipetted 0.1 ml of a $3.0 \times 10^4$ cells/ml suspension of Hela S3 cells (ATCC HTB22) in DEM medium containing 10% of fetal calf serum (manufactured by Nissui, hereinafter referred to as "medium A"). This plate was incubated in a carbon dioxide gas incubator at 37° C. for 20 hours. Then, 0.1 ml of the test compound, which had been appropriately diluted with the medium A, was added to each well followed by incubation in the carbon dioxide gas incubator at 37° C. for additional 72 hours. After having removed the culture supernatant, the residue was washed with physiological saline once and treated with 0.1 ml of methanol for 10 minutes to thereby fix the cells. Next, the cells were stained with 0.1 ml of Giemsa's staining solution [stock solution for Giemsa's staining Merck Art 9204 (manufactured by Merck): physiological saline=1:10] for 5 minutes. After having removed the staining solution, the residue was washed with 0.2 ml of water once. Then, the pigment was extracted with 0.2 ml of 0.1N hydrochloric acid, and the absorbance was measured at 620 nm by the use of a microplate reader. From the result of the measurement, the increased amount of the grown cells was determined. By comparing the absorbance of the cells treated with the test compound of a known concentration with that of the untreated cells, the 50% inhibitory concentration ($IC_{50}$) of the test compound against the cell growth was calculated. Table 2 shows the results.

TABLE 2

| Compound | $IC_{50}$ (µM) |
|---|---|
| UCH15A | 1.2 |
| UCH15B | 1.0 |

Test Example 3

Antitumor Activity on Sarcoma 180 Tumor

Male ddY mice were used herein, which were grouped into plural groups, each group being comprised of 5 mice. $5 \times 10^6$ sarcoma 180 tumor cells were implanted into the subcutaneous tissue in the axillary region of each mouse. On the 1st day after the implantation, a solution of UCH15B dissolved in physiological saline was injected once into the tail vein of each mouse. On the 7th day after the implantation, the mean tumor volume (mm$^3$) in each mouse was measured. From the result of measurement, the antitumor activity of the compound UCH15B was determined. Said antitumor activity was calculated according to the following equation.

Antitumor Activity

=[mean tumor volume (mm$^3$) in mice in test group]/[mean tumor volume (mm$^3$) in mice in control group (to which was administered physiological saline only)]

The results are in Table 3.

TABLE 3

| Compound | Dose (mg/kg) | Mean Tumor Volume (mm$^3$) | Antitumor Activity (T/C) |
|---|---|---|---|
| UCH15B | 0 (control) | 2340 | 1 |
|  | 0.094 | 1528 | 0.65 |
|  | 0.19 | 1405 | 0.60 |
|  | 0.38 | 1035 | 0.44 |
|  | 0.75 | 522 | 0.22 |

Test Example 4

Antitumor Activity on Human Ovarian cancer strain A2780

Nude mice (BALB/C-nu/nu) were used herein, which were grouped into plural groups, each group being comprised of 5 mice. A human ovarian cancer strain A2780 tumor (a piece of 8mm$^3$) was implanted into the subcutaneous tissue in the abdominal region of each mouse. After the implantation, when the tumor volume in each tumor-carrying mouse reached between 50 and 300 mm$^3$, a solution of UCH15B in physiological saline was injected once into the tail vein of each mouse (in the test group). Just before the injection of said UCH15B solution, the volume of the tumor ($V_0$) in each mouse was measured. 14 days after the injection thereof, the volume of the tumor (V) therein was measured. Into each mouse in the control group, only physiological saline was injected. Just before the injection of physiological saline, the volume of the tumor ($C_0$) in each mouse was measured. 14 days after the injection thereof, the volume of the tumor (C) therein was measured. The antitumor activity of the test compound, UCH15B was obtained according to the following equation.

Antitumor Activity=[V/V0]/[C/C$_0$]

V: tumor volume (mm$^3$) in test group after the test $V_0$: tumor volume (mm$^3$) in test group before the test C: tumor volume (mm$^3$) in control group after the test $C_0$: tumor volume (mm$^3$) in control group before the test The results are shown in Table 4.

TABLE 4

| Compound | Dose (mg/kg) | Antitumor Activity (T/C) |
|---|---|---|
| UCH15B | 0 (control) | 1 |
|  | 0.38 | 0.27 |

Now, examples of the present invention are given below.

BEST MODES FOR CARRYING OUT THE INVENTION

EXAMPLE 1

Streptomyces sp. UCH15 strain (FERM BP-5082) was used as a seed strain. This strain was inoculated into 300 ml of a seed medium (pH 7.2 before sterilization), which was composed of 10 g/liter of glucose, 10 g/liter of soluble starch, 5 g/liter of bactotryptone (manufactured by Difco), 5 g/liter of yeast extract, 3 g/liter of meat extract, and 0.5 g/liter of magnesium phosphate, in a 2-liter Erlenmeyer flask, and cultivated with shaking at 200 rpm at 28° C. for 48 hours. 900 ml of the seed culture thus obtained was transferred into 18 liters of a fermentation medium having the following composition in a 30-liter jar fermenter, and incubated therein under aeration/agitation (400 rpm, aeraton rate: 18 liters/min) at 25° C.

Composition of Fermentation Medium: 50 g/liter of glycerol, 15 g/liter of dry yeast, 0.5 g/liter of $KH_2PO_4$, 0.5 g/liter of $Mg_3(PO_4)_2 \cdot 8H_2O$ (pH 7.0 before sterilization, adjusted with NaOH)

The cultivation was continued for 42 hours without particularly regulating the pH value of the medium. Then, the culture was filtered to separate the cells from the cultured medium. The cultured medium was passed through a chromatography column with Diaion HP-20, to absorb the active component. The impurities were removed by applying methanol-water (3:7, v/v) to the column, and the active component was eluted with methanol/water (4:6, v/v). The active fraction thus eluted was concentrated, and passed through a chromatography column with Diaion HP-20SS, to absorb the active component. The impurities were removed by applying methanol/water (3:7, v/v) to the column. Then, the active component was eluted with methanol/water (4:6, v/v). The active fraction thus eluted was concentrated, and then purified through high performance liquid chromatography (HPLC) under the conditions mentioned below, in which the fraction was developed with developers of 5 to 10% acetonitrile/0.5% trifluoroacetic acid (TFA). Thus a fraction containing UCH15B (retention time: 26 min) and a fraction containing UCH15A (retention time: 30 min) were obtained separately. Each fraction was concentrated and further fractionated through HPLC, and the resulting active fraction was concentrated and then lyophilized. Thus 2.5 mg of UCH15A and 10 mg of UCH15B were obtained as white solids.

HPLC Conditions:
   Column: Develosil ODS-HG-5 (manufactured by Nomura Chemical)
   Eluent: 5 to 10% acetonitrile
   Flow Rate: 10 ml/min
   Detection: 300 nm
   Retention Time:
      UCH15B: 27 min
      UCH15A: 30 min
Industrial Applicability According to the present invention, provided are UCH15 compounds having excellent antibacterial and antitumor activities.

We claim:
1. UCH15 compounds of the formula (I):

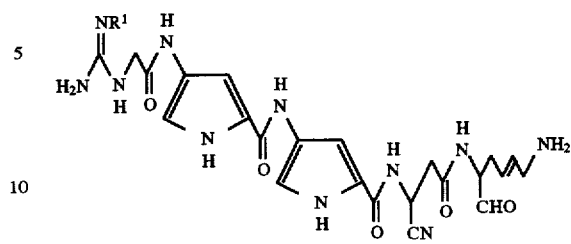

wherein $R^1$ represents a hydrogen atom or a hydroxyl group.

* * * * *